United States Patent [19]
Simon

[11] Patent Number: 5,182,857
[45] Date of Patent: Feb. 2, 1993

[54] SHAVING APPARATUS

[75] Inventor: Pal Simon, Warstein, Fed. Rep. of Germany

[73] Assignee: U.S. Philips Corp., New York, N.Y.

[21] Appl. No.: 679,077

[22] PCT Filed: Oct. 29, 1990

[86] PCT No.: PCT/EP90/01929
§ 371 Date: Sep. 3, 1991
§ 102(e) Date: Sep. 3, 1991

[87] PCT Pub. No.: WO91/06406
PCT Pub. Date: May 16, 1991

[30] Foreign Application Priority Data
Nov. 2, 1989 [DE] Fed. Rep. of Germany ....... 3936367

[51] Int. Cl.⁵ ............................................. A61B 17/00
[52] U.S. Cl. .................................... 30/34.05; 30/140; 132/118; 606/9
[58] Field of Search .................. 30/140, 32, 34.05; 606/9, 19, 13; 132/118

[56] References Cited
U.S. PATENT DOCUMENTS

| | | | |
|---|---|---|---|
| 3,693,623 | 9/1972 | Harte et al. | 606/9 |
| 4,617,926 | 10/1986 | Sutton | 606/9 |
| 4,819,669 | 4/1989 | Politzer | 132/118 |
| 5,057,104 | 10/1991 | Chess | 606/9 |
| 5,059,192 | 10/1991 | Zaias | 606/9 |
| 5,065,515 | 11/1991 | Iderosa | 30/140 |

FOREIGN PATENT DOCUMENTS 3220962 12/1983 Fed. Rep. of Germany .......... 606/9

OTHER PUBLICATIONS

"The Laser Razor" at p. 38 of The Space Age Razor Race, Jaffe et al., MAD, Band. 208, Jul. 1979.

Primary Examiner—Douglas D. Watts
Assistant Examiner—Hwei-Siu Payer
Attorney, Agent, or Firm—Ernestine C. Bartlett

[57] ABSTRACT

The invention relates to a shaving apparatus which is characterized in that a laser beam (13) serves as the cutting means, and to a method of removing body hairs by means of such a shaving apparatus. The shaving apparatus comprises a shear plate (11) with an entry slot (24). The laser beam (13) is generated by a device (12), severs the hair in the proximity of the entry slot, and is preferably reflected from the shear plate and detected by a photo-cell (18). The shaving apparatus in accordance with the invention enables body hairs to be severed without irritating the skin.

10 Claims, 3 Drawing Sheets

SHAVING APPARATUS

FIELD OF THE INVENTION

The present invention relates to a shaving apparatus. The prior-art shaving apparatus are either mechanical wet-shavers, which sever the hair by means of a razor blade, or electrical shaving apparatus with vibrating or rotating shaving devices. All known shaving apparatus have the disadvantage that during shaving the blades or shaving devices not only sever the hair but also come into contact with the skin and thereby irritate the skin. In addition, small skin particles are often removed locally in the process of shaving, which increases the likelihood of infection.

SUMMARY OF THE INVENTION

An object of the present invention is provide a shaving apparatus in which the cutting means acts upon the hair but does not come into contact with the skin, so that this disadvantage is eliminated.

This object is achieved by means of a shaving apparatus in which a laser beam acts as a cutting means. By means of laser technology it is possible to generate an accurately directed laser beam which severs the hair by burning, without any contact with the skin. In accordance with a preferred feature of the invention a laser beam is generated whose frequency corresponds to the absorption frequency of the hair substance. The hair contains pigment so that the laser beam is absorbed effectively in the corresponding frequency range. This absorption frequency differs from those of the basic constituents of the human skin. The skin is not burned upon incidence of a laser beam of this frequency. However, the shaving apparatus in accordance with the invention is constructed in such a manner that contact of the laser beam with the skin is substantially impossible. In accordance with the invention the shaving apparatus comprises a housing with a shear plate. This shear plate, which may be flat or curved, has a comparatively narrow slot through which the hair to be severed enters the interior of the housing when the shear plate of the shaving apparatus is moved over the skin. The laser beam is then generated inside the housing and impinges on the inner side of the shear plate, preferably in the proximity of the entry slot, where it acts upon the hair. Preferably, the zone where the laser beam is incident is reflecting, so that the beam is locally reflected. The reflected laser beam can be detected by a photo-cell arranged in the housing. If an obstacle inadvertently enters the entry slot and the path of the laser beam this beam is interrupted. This interruption is detected by the photo-cell and transferred to a switching device to turn off the laser beam. This provides a safety device which is activated in particular when the shaving apparatus is not handled properly. As the laser energy is preferably focused by an optical system, a distinct thermolytic effect, i.e. the cutting action, is obtained at a comparatively low power. Preferably, the generated laser beam is planar and is suitably generated as a flat layer with a minimal dimension in a direction perpendicular to its plane, which is preferably aligned with the edge of the entry slot parallel to the slot. Generating such a curtain-like laser beam by means of laser technology is possible without any problem. Thermal conduction allows the hairs to be shortened beyond the point of incidence of the laser beam.

Since the removal of hairs by burning with the aid of the laser beam may not be odorless an odor filter may be provided in the housing of the shaving apparatus. In addition, a fan may be arranged in the housing which draws in the air to be passed through the odor filter. Preferably, the width of the entry slot is between approximately 0.2 mm and 1.0 mm and is, for example, in the range of approximately 0.5 mm. The shaving apparatus in accordance with the invention may serve for the daily removal of facial hairs or for the removal of other body hairs, for example for applications particularly in the medical field.

The present invention also relates to a method of removing body hairs, in which the body hairs are severed by means of a laser beam, in particular by means of a shaving apparatus as characterized in any one of the appended claims.

BRIEF DESCRIPTION OF THE DRAWING

The invention will now be described in more detail hereinafter with reference to the accompanying drawings. in which.

DETAILED DESCRIPTION OF THE PREFERRED EMBODIMENTS

Figure 1:
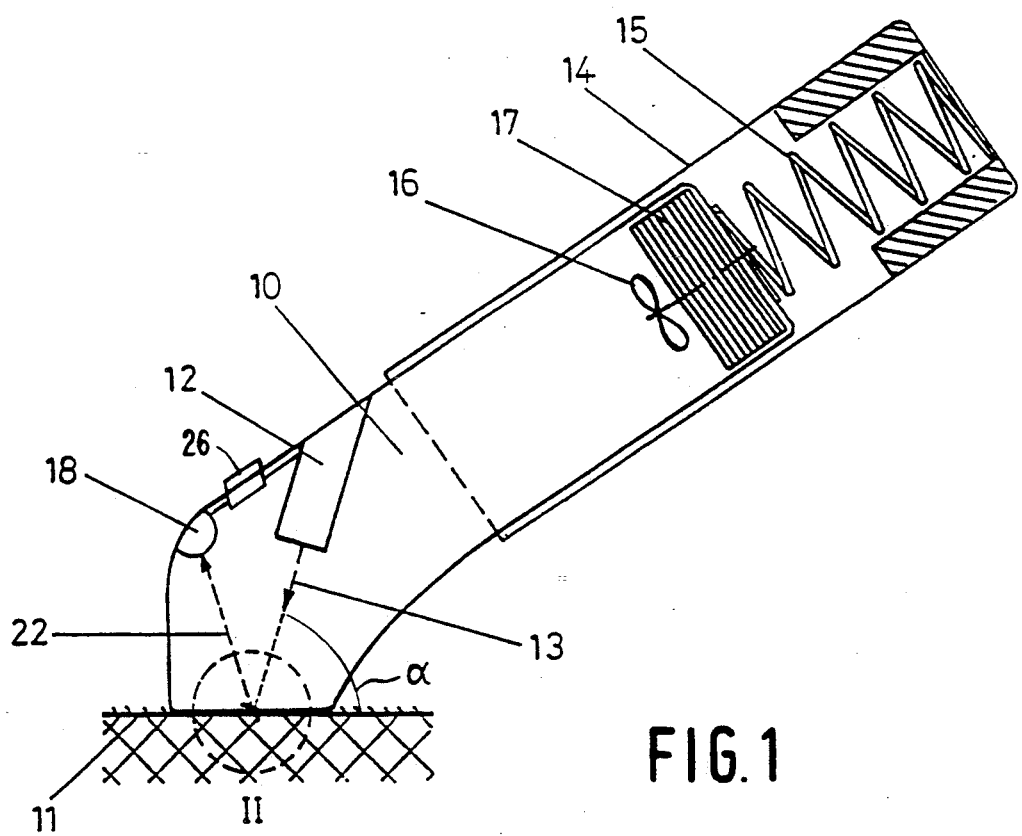
FIG. 1 is a diagrammatically simplified longitudinal sectional view of a shaving apparatus in accordance with the invention.

With reference to FIG. 1, the shaving apparatus in accordance with the invention comprises a housing with a lower housing section 10 and an upper housing section 14, the upper housing section 14 engaging over the lower housing section and being guided on the latter so as to be axially movable against the force of a spring 15. A device 12 which generates the laser beam 13 (laser gun) is situated in the lower part on the upper housing wall in the housing section 10. The laser gun is powered either by a battery or with mains current, the current supply not being shown in FIG. 1. The upper part of the housing section 10 accommodates a fan 16, which extracts the exhaust air, and an odor filter 17 or odour suppressor, which extracted air may be discharged by means not shown in FIG. 1. As is apparent from FIG. 1 in combination with FIG. 2, the laser beam 13 generated by the laser gun 12 impinges on a reflecting zone 23 of the shear plate 11 and is reflected from this zone, the angle of incidence $\alpha$ between the laser beam (13) and the shear plate being preferably about 50° to 85°. The reflected beam 22 is incident on a photo-cell 18 which is situated on the housing wall and which is connected to a switching device 26. The human hair is so small that when it enters the radiation path of the laser beam it is not detected as an obstacle by the photo-cell 18.

Figure 2:
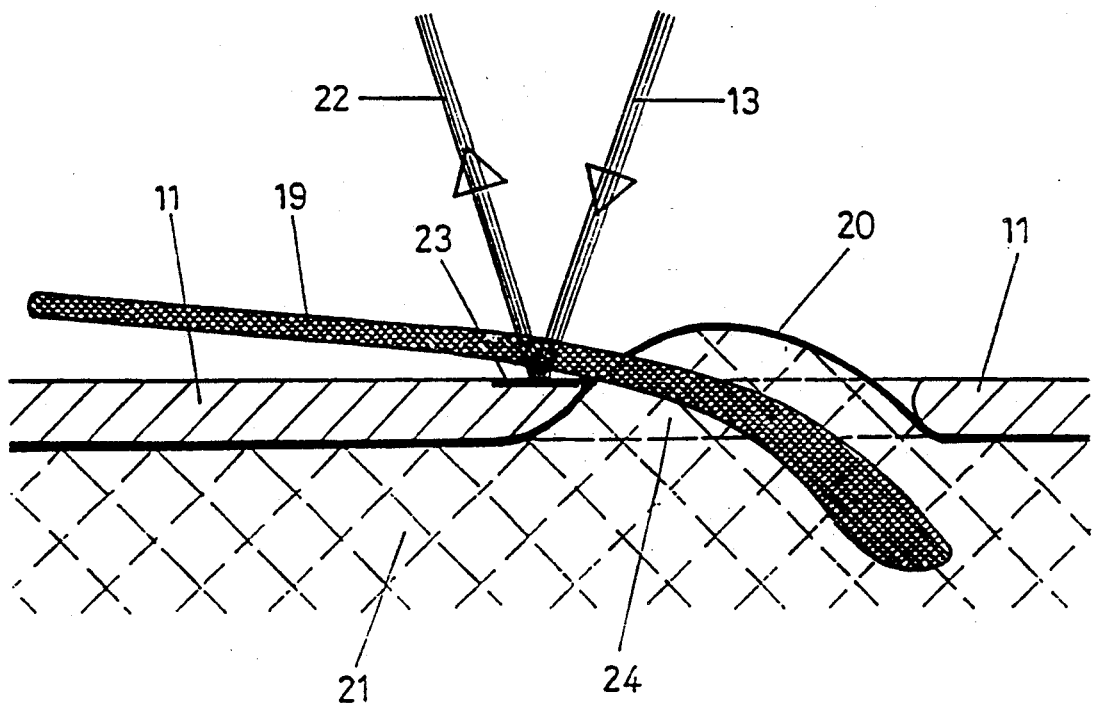
FIG. 2 is an enlarged-scale sectional view of the shear plate.

2 illustrates that the shear plate 11 in contact with the skin 20 to be shaved. The shear plate 11 has a slot which extends perpendicularly to the plane of drawing and which has a width of, for example, approximately 0.5 mm. Since the shear plate 11 of the shaving apparatus is applied with some pressure and is then moved over the skin the tissue underneath the skin forms a fold or bulge which projects into the slot 24 in the shear plate. The hairs 19 in this skin area thus project into the interior of the housing. FIG. 2 shows such a hair 19 by way of illustration.

Figure 3:
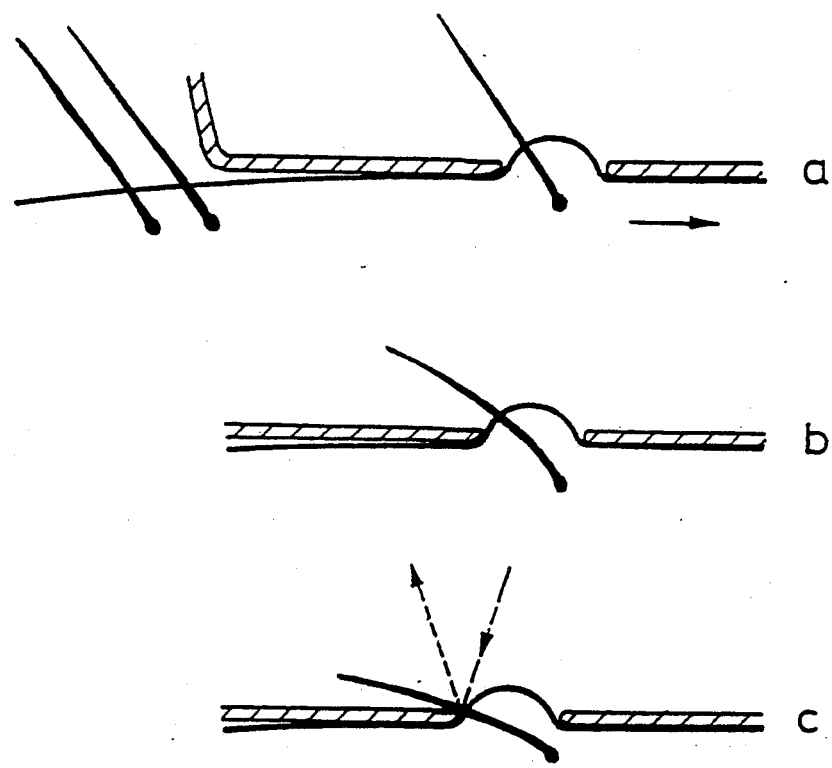
FIG. 3 illustrates the operating principle of the shaving apparatus in accordance with the invention.

FIGS. 2 and 3 illustrate how a hair is severed by means of the shaving apparatus in accordance with the invention. FIG. 3 shows diagrammatically a hair in three different positions a, b and c when, viewed in the Figure, the shear plate is moved to the right over the skin. The diagram c shows that the hair, when it contacts the slightly pointed left-hand edge of the slot in the shear plate, is situated inside the housing of the shaving apparatus and is inclined at a comparatively acute angle relative to the shear plate. In this situation corresponding to the diagram c, the laser beam 13 (see FIG. 2) impinges on the hair near the root of the hair via the reflecting zone 23 adjacent the edge of the slot. Preferably, the laser beam is inclined at a steep angle relative to the hair to be severed, and in the ideal case the angle is 90° when the hair is severed by the laser beam. As is further apparent from FIG. 2 the hair is then severed but the laser beam is not incident on the skin portion 20 which bulges through the slot 24. All the hairs projecting into the slot in the shear plate 11 are severed in a similar manner.

Figure 4:
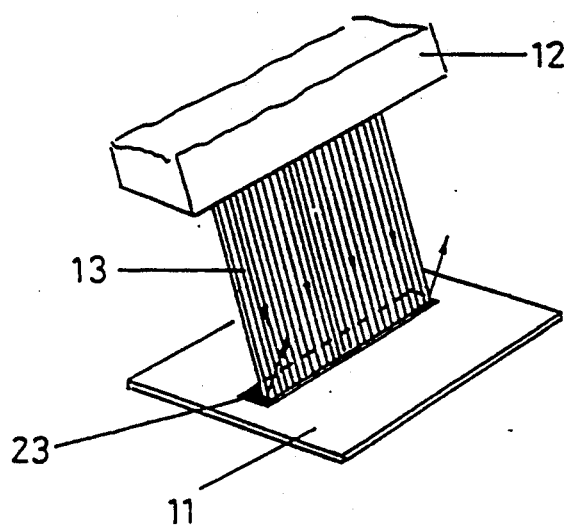
FIG. 4 is a perspective view showing the shape of the generated laser beam.

FIG. 4 shows the flat shape of the laser beam 13, which is substantially curtain-shaped and is oriented precisely parallel to the slot 24 in the shear plate. Thus, the laser beam 13 is a planar beam which intersects the shear plate 11 in the reflecting zone 23 as a line of only very small width.

Figure 5:
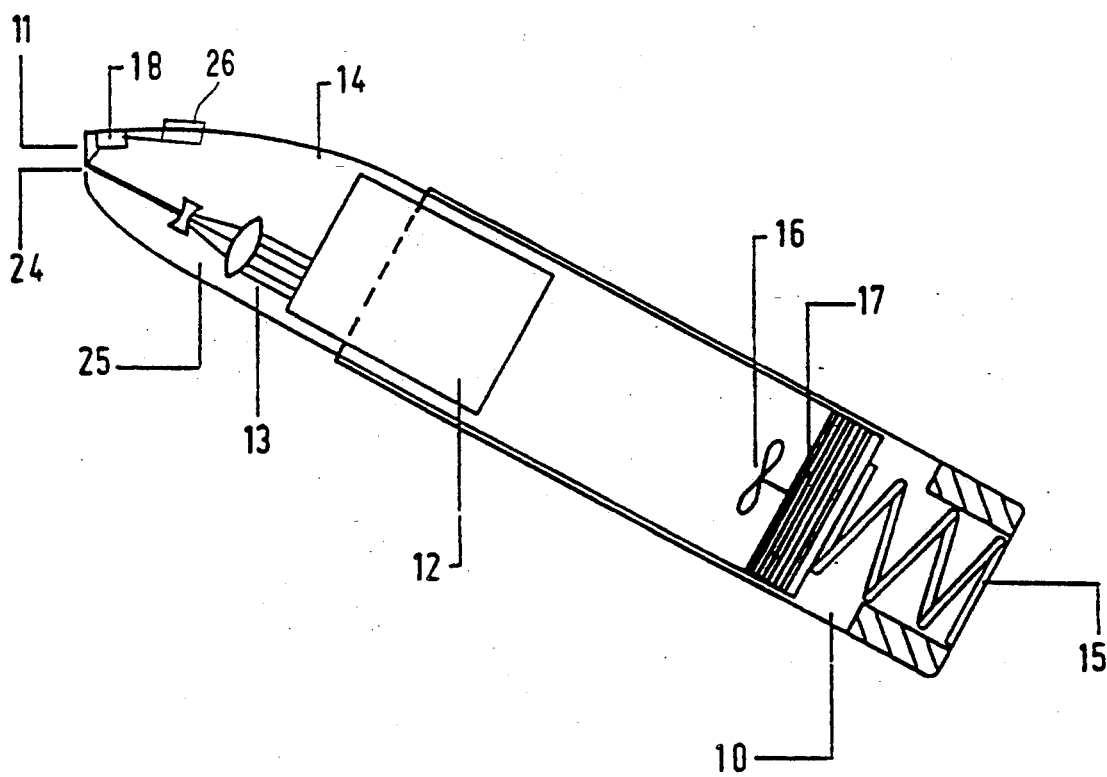
FIG. 5 is a diagrammatically simplified longitudinal sectional view of a shaving apparatus in accordance with an alternative embodiment of the invention.

In an alternative embodiment of the invention shown in FIG. 5, the shape of the housing is slightly different and the shear plate is narrower. Moreover, there is provided an optical system 25 by which the generated laser beam is focused and directed so as to be incident as a focussed high-energy beam on the inner side of the shear plate adjacent the entry slot. The photo-cell is arranged in the housing tip nearer the zone of incidence of the laser beam. The device for generating the laser beam is disposed axially inside the housing and with this arrangement it can be dimensioned to suit specific requirements.

I claim:

1. A shaving apparatus comprising a housing (10) and a shear plate (11) with a hair entry slot (24) wherein inside the housing (10) there is provided a device (12) for generating a laser beam (13) which acts as a cutting means and which impinges on the inner side of the shear plate (11) in the proximity of the entry slot (24) where it acts upon and severs the hair, said laser beam (13) impinging on said shear plate (11) and being reflected along the entry slot (24) in a reflecting zone of incidence (23) on the shear plate (11).

2. A shaving apparatus as claimed in claim 1, wherein the laser beam (22) which is reflected from the reflecting zone (23) of incidence is detected by a photo-cell (18) arranged on the inner side of the housing.

3. A shaving apparatus as claimed in claim 2 wherein the photo-cell (18) is connected to a switching device adapted to turn off the laser beam (13).

4. A shaving apparatus as claimed in claim 1 wherein the device (12) generates a laser beam whose frequency substantially corresponds to the absorption frequency of the hair substance.

5. A shaving apparatus as claimed in claim 1 wherein there is provided an optical system by means of which the generated laser beam is directed.

6. A shaving apparatus comprising a housing (10) and a shear plate (11) with a hair entry slot (24) wherein inside the housing (10) there is provided a device (12) for generating a laser beam (13) which acts as a cutting means and which impinges on the inner side of the shear plate (11) in the proximity of the entry slot (24) where it acts upon and severs the hair, there being an angle of incidence $\alpha$ between the laser beam (13) and the shear plate (11) of between 50° and 85°.

7. A shaving apparatus comprising a housing (10) and having upper and lower housing sections and a shear plate (11) with a hair entry slot (24) wherein inside the housing (10) there is provided a device (12) for generating a laser beam (13) which acts as a cutting means and which impinges on the inner side of the shear plate (11) in the proximity of the entry slot (24) where it acts upon and severs the hair, said upper housing section (14) engaging over said lower housing section and the lower housing section being guided in the upper housing section so as to be axially movable against the force of a spring (15).

8. A shaving apparatus comprising a housing (1) and a shear plate (11) with a hair entry slot (24) wherein inside the housing (1) there is provided a device (12) for generating a laser beam (13) which acts as a cutting means and which impinges on and is reflected along the inner side of the shear plate (11) in the proximity of the entry slot (24) where it acts upon and severs the hair, a fan (16) being arranged in the housing.

9. A shaving apparatus as claimed in claim 8, wherein in the housing there is provided a filter device to filter the air drawn into the housing by the fan (16).

10. A shaving apparatus comprising a housing (10) and a shear plate (11) with a hair entry slot (24) wherein inside the housing (10) there is provided a device (12) for generating a laser beam (13) which acts as a cutting means and which impinges on the inner side of the shear plate (11) in the proximity of the entry slot (24) where it acts upon and severs the hair, the generated laser beam (13) being planar and impinging on the shear plate (11) and is reflected along a line parallel to the edge of the entry slot (24).

* * * * *